US009238101B2

(12) United States Patent
Hariharesan et al.

(10) Patent No.: US 9,238,101 B2
(45) Date of Patent: Jan. 19, 2016

(54) INFUSION PUMP CASSETTE WITH ANTI-FREE-FLOW VALVE MECHANISM

(75) Inventors: Seralaathan Hariharesan, Flower Mound, TX (US); Brian Highley, Southlake, TX (US)

(73) Assignee: Nestec S.A., Vevey (CH)

( * ) Notice: Subject to any disclaimer, the term of this patent is extended or adjusted under 35 U.S.C. 154(b) by 238 days.

(21) Appl. No.: 13/147,099

(22) PCT Filed: Jan. 22, 2010

(86) PCT No.: PCT/US2010/021721
§ 371 (c)(1),
(2), (4) Date: Sep. 6, 2011

(87) PCT Pub. No.: WO2010/088143
PCT Pub. Date: Aug. 5, 2010

(65) Prior Publication Data
US 2011/0313358 A1    Dec. 22, 2011

Related U.S. Application Data

(60) Provisional application No. 61/148,863, filed on Jan. 30, 2009.

(51) Int. Cl.
*A61M 1/00* (2006.01)
*F04B 43/12* (2006.01)
(Continued)

(52) U.S. Cl.
CPC ....... *A61M 5/14232* (2013.01); *A61M 5/14228* (2013.01); *F04B 43/12* (2013.01); *A61M 39/281* (2013.01); *A61M 2205/128* (2013.01); *A61M 2205/14* (2013.01); *A61M 2205/6045* (2013.01)

(58) Field of Classification Search
CPC ..................... A61M 5/14232; A61M 5/14228; A61M 39/281; A61M 2205/14; A61M 2205/128; A61M 2205/12
USPC ............. 604/131, 151, 153; 417/474–477.14, 417/477.2
See application file for complete search history.

(56) References Cited

U.S. PATENT DOCUMENTS 4,025,241 A * 5/1977 Clemens ............. F04B 43/1284
                                                              417/477.11
4,886,431 A * 12/1989 Soderquist .......... F04B 43/1292
                                                              417/477.11
(Continued)

FOREIGN PATENT DOCUMENTS

DE        10348653        5/2005
EP        1557187         7/2005
(Continued)

OTHER PUBLICATIONS

Search Report for International Application No. PCT/US2010/021721 mailed Apr. 23, 2010.

*Primary Examiner* — Bhisma Mehta
*Assistant Examiner* — Jenna Zhang
(74) *Attorney, Agent, or Firm* — K&L Gates LLP

(57) ABSTRACT

A cassette (1) that is insertable into an infusion pump for delivery of a fluid to a subject that has a housing with two ends for holding flexible tubing (75) through which the fluid is directed. The housing has an open area exposing the tubing, which engages a pumping mechanism when inserted into an infusion pump. An anti-flow valve mechanism (100) associated with the tubing or the cassette and present either in, on or near the housing is made up of a piston (103/105) and spring (110), where the spring biases the piston against the tubing to prevent fluid flow.

16 Claims, 6 Drawing Sheets

(51) Int. Cl.
*A61M 5/142* (2006.01)
*F04B 43/08* (2006.01)
*F04B 43/06* (2006.01)
*A61M 39/28* (2006.01)

(56) References Cited

U.S. PATENT DOCUMENTS

| | | | |
|---|---|---|---|
| 5,213,483 A | | 5/1993 | Flaherty et al. |
| 5,257,917 A | * | 11/1993 | Minarik ............. F04B 43/1292 417/475 |
| 5,437,635 A | | 8/1995 | Fields et al. |
| 5,586,868 A | * | 12/1996 | Lawless ............ A61M 5/14224 128/DIG. 12 |
| 5,601,420 A | * | 2/1997 | Warner ............. A61M 5/14228 128/DIG. 12 |
| 5,709,539 A | * | 1/1998 | Hammer ............ F04B 43/1253 417/477.11 |
| 5,904,668 A | * | 5/1999 | Hyman ................ A61M 5/142 604/131 |
| 6,165,154 A | | 12/2000 | Gray et al. |
| 6,203,528 B1 | * | 3/2001 | Deckert ................ A61M 5/142 604/131 |
| 2007/0265559 A1 | * | 11/2007 | Kunishige ........... A61M 39/281 604/7 |
| 2009/0087327 A1 | * | 4/2009 | Voltenburg, Jr. .. A61M 5/14232 417/477.2 |

FOREIGN PATENT DOCUMENTS

| | | |
|---|---|---|
| EP | 161588 | 1/2006 |
| JP | S54103290 | 8/1979 |
| JP | H0126304 | 5/1989 |
| JP | 2007505707 | 3/2007 |
| WO | WO 9813080 | 4/1998 |
| WO | WO 03097156 | 11/2003 |
| WO | WO2004087239 | 10/2004 |
| WO | WO2006068070 | 6/2006 |
| WO | WO2007033025 | 3/2007 |
| WO | WO2009042181 | 4/2009 |

\* cited by examiner

INFUSION PUMP CASSETTE WITH ANTI-FREE-FLOW VALVE MECHANISM

CROSS REFERENCE TO RELATED APPLICATIONS

The present application is a National Stage of International Application No. PCT/US2010/012721, filed on Jan. 22, 2010, which claims priority to U.S. Provisional Application No. 61/148,863, filed on Jan. 30, 2009, the entire contents of each of which are being incorporated herein by reference.

BACKGROUND

The present invention relates to an apparatus and method for preventing free flow during enteral or parenteral administration of solutions through the tubing of an infusion line. More particularly, the present invention relates to a device that can be associated with an infusion pump for delivery of a fluid to a subject wherein the device includes an anti-flow valve mechanism such that, when the device is associated with an infusion pump, fluid is allowed to flow through the tubing, and when removed from the pump the anti-flow valve closes off the tubing to prevent the undesirable free-flow of solution therethrough.

The use of infusion sets to administer solutions to patients is well known in the medical arts. Infusion sets are used for both enteral and parenteral applications. Enteral feeding pumps are used to provide patients with nutrition and medication when they are unable, for a variety of reasons, to eat normally. Parenteral (intravenous) solutions are provided to patients to ensure adequate hydration and to provide needed nutrients, minerals and medication. Often, the infusion set is placed in a free standing arrangement in which gravity forces the solution into the patient. To prevent this, the tubing is often clamped or otherwise blocked to prevent such flow when not desired.

In many medical applications, fluids must be administered to a subject in a well regulated manner. In such instances, a free-standing infusion arrangement, where fluids are delivered to the patient under the force of gravity, is not acceptable. Instead the fluids are administered through the use of an infusion pump. An infusion pump is used to regulate the amount and rate at which the fluid is delivered from a reservoir to the patient. Typically a tube connected to the reservoir passes through the infusion pump and is intravenously inserted into the patient. While the tubing from the reservoir is in the infusion pump, free flow of the fluid is restricted by the pressure of the pump mechanism rollers closing off the tubing, however, when the tubing is removed from the pump, this pressure is released and fluid flow may resume under gravity. Devices that suffer from this disadvantage are those which lack a flow control mechanism. To prevent such free-flow of fluids, multiple means of closing the tubing off when it is not inserted in a pump have been disclosed in the prior art. These devices can be manually operated clamps, or cassettes with some form of automatic flow control mechanism.

For proper operation, the clamped or otherwise blocked tubing must be manipulated so that it allows fluid flow therethrough. It is not uncommon, however, for emergencies or other distractions to prevent the medical personnel from properly loading or unloading infusion sets into the feeding pump. When the infusion set is not properly loaded in the pump or is improperly removed and the tubing is opened to allow fluid flow, a free-flow situation often develops, wherein an amount of solution that is many times the desired dose can be supplied to the patient within a relatively short time period. This can be particularly dangerous if the solution contains potent medicines or if the patient's body is not physically strong enough to adjust to the large inflow of solution.

Numerous devices have been developed in an attempt to prevent free flow conditions. Such devices, however, typically add significantly to the overall cost of the infusion set and some provide only marginal protection against free flow. Furthermore, some of these are complicated making it difficult for medical personnel to properly operate them.

One attempted simplification of such systems is the use of an infusion cassette that is only operable to allow fluid flow through the tubing when the cassette is inserted into the pump. Cassette devices of the types like those disclosed in U.S. Pat. No. 5,904,668 to Hyman et al., and U.S. Pat. No. 6,165,154 to Gray et al. tend to be more complex and require the action of additional associated mechanisms, such as the movement or closing of an infusion pump door, handle or the like to function fully.

Thus, there is a need for infusion pumps and cassettes that provide improved performance over the art in that they need to be less complex and easier to use to quickly and conveniently control the delivery of fluids to the patient. The present invention now satisfies this need.

SUMMARY OF THE INVENTION

One embodiment of the invention relates to a cassette for engagement with an infusion pump for delivery of a fluid to a subject. This cassette comprises a housing having first and second ends for holding flexible tubing through which the fluid is directed, wherein the tubing is configured for engaging a pumping mechanism of an infusion pump that provides movement of fluid through the tubing; and an anti-flow valve mechanism associated with the tubing, housing or the cassette and present either in or near the housing or cassette. The anti-flow valve mechanism is biased against the tubing in a fluid non-delivery position to prevent flow therethrough and includes a member operatively associated with the cassette and anti-flow valve mechanism to overcome the force-applying member bias to allow flow of fluid through the tubing when the housing is engaged with the pump. The anti-flow valve mechanism is associated with the tubing, cassette or housing or is situated in or near the cassette or housing. The anti-flow valve mechanism preferably comprises a moveable member and a force-applying member, wherein the force-applying member in a fluid non-delivery position biases the moveable member against the tubing to prevent flow therethough. The cassette also includes a tab member operatively associated with the cassette housing and anti-flow valve mechanism and movable between the fluid non-delivery position and a fluid delivery position where the force-applying member bias is removed so as to allow flow of fluid through the tubing. The tab member is operatively associated with the cassette and anti-flow valve mechanism so as to overcome the force-applying member bias. The housing is configured and dimensioned for engagement with a dedicated infusion pump, wherein during or after engagement the tab member is moved to the fluid delivery position by the pump to allow flow of the fluid through the tubing, while before or as the cassette is removed from the pump, the tab member is released so that the force-applying member returns to the fluid non-delivery position to prevent flow of fluid through the tubing.

In this cassette, the tab member can move the moveable member to the fluid delivery position as the cassette engages the infusion pump to allow flow of fluid through the tubing and as the cassette is removed from the pump the tab member is released so that the moveable member returns to the fluid non-delivery position to prevent flow of fluid through the tubing such that movement of the tab member between the fluid non-delivery position and the fluid delivery position changes the biasing of the force-applying member. Alternatively, the tab member can move the moveable member to the fluid delivery position after the cassette engages the infusion pump to allow flow of fluid through the tubing, and before the cassette is removed from the pump the tab member is released.

The housing of the cassette preferably has an essentially rectangular shape and is configured and dimensioned to fit within an opening in the infusion pump, and the length of tubing is initially held between the ends of the cassette in a straight line and in front of a rigid curved wall of the housing such that when engaged with the pumping mechanism of the pump, the length of tubing is accurately positioned in contact with and between the curved wall and the pumping mechanism.

Advantageously, the force-applying member of the anti-flow valve mechanism includes a compression spring and the moveable member of the anti-flow valve mechanism comprises a pinch head that has a relatively larger cross-sectional surface that contacts the force-applying member and a relatively narrower cross-sectional surface contacting the tubing that concentrates the force of the force-applying member against the tubing. Also, the housing may include registration grooves for alignment of the cassette during engagement with the infusion pump. The housing of the cassette generally includes at least one window adjacent the tubing to allow monitoring or detection of fluid flow therethrough. In a preferred arrangement, the housing is made of molded plastic, the tubing is made of an elastomeric or silicone material, and the tubing is held between inlet and outlet tubing supports in the housing. Each tubing support can include a male junction and a female junction, wherein in the inlet support the male junction is configured and dimensioned to fit inside the tubing and the female junction is configured and dimensioned to receive tubing extending to a fluid supply, and in the outlet support, the male junction is configured and dimensioned to fit inside the tubing and the female junction is configured and dimensioned to receive the length of tubing that extends to the subject.

Another embodiment of the invention relates to a fluid delivery system comprising one of the cassettes described herein and an infusion pump, wherein the pump includes a pump housing having an opening configured and dimensioned to receive or engage with the cassette; and an activation mechanism for engaging the member and thereby causing the member to move between the fluid non-delivery position and the fluid delivery position to allow fluid flow through the tubing, and wherein the pumping mechanism that engages the flexible tubing to provide movement of fluid through the tubing only when the cassette is engaged with the pump, the pump detects the cassette is engaged, and the tab member is in the fluid delivery position.

The pump can have a detector for determining whether the cassette is properly engaged with the pump and pump mechanism. The pumping mechanism typically stretches the flexible tubing by an amount necessary to tension the tubing by a sufficient amount to allow the correct fluid flow through the tubing each time the pumping mechanism and cassette are engaged. Also, the activation mechanism causes the tab member to move between the fluid non-delivery position and a fluid delivery position either as the cassette engages the pump or after the cassette engages the pump. Thus, the pumping mechanism is in a fixed position and the flexible tubing becomes engaged therewith by moving the cassette into contact with the pumping mechanism, or the cassette is in a fixed position when associated with the infusion pump and the pumping mechanism engages the flexible tubing by moving into contact therewith. In certain embodiments, the infusion pump further comprises at least one registration component that engages the registration grooves of the cassette, and at least one sensor in optical alignment with the window of the cassette for monitoring or detection of fluid flow through the tubing.

Yet another embodiment of the invention relates to a method of preventing free flow of fluid through the tubing of an infusion set which comprises providing the tubing in a cassette that engages an infusion pump for delivery of a fluid to a subject, and providing the tubing or cassette with an anti-flow valve mechanism comprising a moveable member and force-applying member wherein, when not engaged with the pump, the moveable member and force-applying member are maintained in a fluid non-delivery position with the force-applying member biasing the moveable member against the tubing to prevent flow therethrough, and further wherein when or after the cassette engages the pump, the force-applying member is moved by the pump to a flow delivery position where the moveable member is not biased against the tubing to allow fluid to flow therethrough.

Also, the invention relates to the use of one of the anti-flow valve mechanisms or fluid delivery systems described herein to prevent free-flow of fluid through the tubing of an infusion set. The anti-flow valve mechanism is provided on or in association with the tubing or a cassette having a housing and can be used for preventing free-flow of fluid through the tubing of an infusion set.

BRIEF DESCRIPTION OF THE DRAWINGS

A preferred embodiment of the present invention, which is illustrative of the best mode contemplated by the applicants, is presented in the drawings and detailed description that follows, wherein.

DETAILED DESCRIPTION OF THE INVENTION

Figure 1:
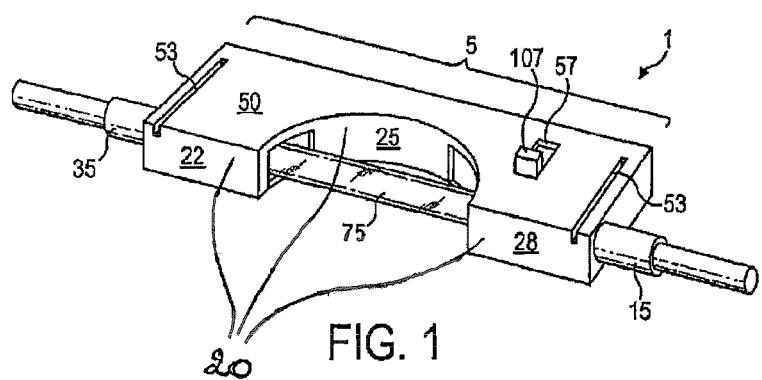
FIG. 1 is a perspective view of the first face, and first and second outside walls of the cassette.

The invention generally relates to a fluid delivery system comprising an infusion pump and a cassette that can be associated with the infusion pump for delivery of a fluid to a subject.

The cassette comprises a housing having first and second ends for holding flexible tubing through which the fluid is directed, wherein the tubing is configured for engaging a pumping mechanism of an infusion pump that provides movement of the fluid through the tubing. The housing has a section with a rigid curved wall adjacent to where the length of tubing engages a pumping mechanism when associated with the infusion pump to provide movement of fluid through the tubing. The cassette may include an anti-flow valve mechanism to prevent free-flow through the tubing when not engaged with the pump.

The cassette can be associated with a dedicated infusion pump that controls the free flow of fluid from a reservoir to a subject, and the cassette/pump fluid delivery system provides controlled delivery of such fluids. The cassette becomes operative through association with the infusion pump, without the interaction of additional independent mechanisms, and restricts fluid flow either prior to or immediately upon removal from the pump. The infusion pump engages the cassette mechanisms to allow a controlled flow of fluid to a patient.

In a first embodiment the invention is directed to a cassette that is connected in between a fluid reservoir such as an IV bag and the intravenous line to the patient. The first embodiment has a housing with an essentially rectangular shape and a width configured and dimensioned to fit within an opening in an infusion pump, where the housing has four outside walls, and two faces.

The first and third outside walls, situated opposite each other, define the first and second ends for holding the tubing through which the fluid is directed. The outside walls forming the first and second ends each have a flat wall with an opening configured and dimensioned to fit either an inlet or outlet tubing support which passes through the opening. In another embodiment, the tubing supports are formed as a single integral part of the housing. The tubing supports thereby being molded features of the housing rather than separate components requiring assembly into the cassette housing.

The flexible tubing is fitted over the male junctions of the tubing supports and held between the ends of the cassette in a straight line. The position of the tubing crosses a section of the housing that can be either exposed or covered.

A second outside wall between and perpendicular to the first and third outside walls has two straight wall sections and a rigid curved wall section located between the two straight wall sections, defining a section with a rigid curved wall adjacent to where the length of tubing engages a pumping mechanism when associated with the infusion pump to provide movement of fluid through the tubing. The rigid curved wall is configured and dimensioned to allow the pumping mechanism of the infusion pump to freely rotate, and has an opening on either side through which the flexible tubing can pass. When associated with the pump, the length of tubing is positioned in contact with and between the curved wall and the pumping mechanism. The curved wall must be suitably strong and rigid to sustain the repeated action of the pumping mechanism.

The housing has a first face in a perpendicular relationship with the outside walls. The first face can be rectangularly configured and dimension to match the outside dimensions of the four walls of the housing, or have a cut-away portion that is configured and dimensioned to coincide with the curved wall section of the third outside wall. The first face has registration groves configured and dimensioned to receive a matching raised portion of the infusion pump, and an opening through which a tab member can protrude.

The housing has a second face in a perpendicular relationship with the outside walls on the side opposite the first face, that can be rectangularly configured and dimension to match the outside dimensions of the four walls of the housing, or have a cut-away portion that is configured and dimensioned to coincide with the curved wall section of the third outside wall. The first and second faces with cut-away portions thereby forming an open area that exposes the tubing, whereas the rectangular faces cover and protect the tubing. The second face has at least one opening, but preferably two openings placed at opposite ends of the housing. The openings are aligned with the position of the tubing and act as windows to allow observation of the fluid and the presence of any bubbles or foreign material. This is particularly important when the tubing in the curved section is covered by both faces thereby preventing viewing of that segment of tubing.

The cassette has an anti-flow valve mechanism associated with the housing comprising a moveable member and a force-applying member. The moveable member comprises a pinch head and a tab member that extends perpendicular to the orientation of the moveable member and a force-applying member through the opening in the first face of the housing. The force-applying member biases the moveable member against the tubing to prevent fluid flow when the cassette is not associated with the infusion pump. The force-applying member used to bias the moveable member can be a compression spring, a leaf spring, or an elastic component. The moveable member has a larger surface on the side contacting the force-applying member, and a narrower surface on the side contacting the tubing. The narrower surface acts to concentrate the force of the force-applying member, and improves the closing action of the moveable member on the tubing. The overall configuration of the moveable member and pinch head can have several shapes, the most preferred being either "T-shaped" or "wedge-shaped." The moveable member can also have a seating opposite the end pressing against the tubing, which holds the force-applying member in position.

The tab member is operatively associated with the housing and anti-flow valve mechanism, and is movable between the fluid non-delivery position and a fluid delivery position. When the cassette is associated with the pump, the tab is pushed back, thereby retracting the associated moveable member from contact with the flexible tubing, and increasing the stored force in the force-applying member. When the cassette is disassociated from the infusion pump, the stored force in the force-applying member is released and returns the moveable member and associated tab member to the biased fluid non-delivery position.

The tab member can also be designed to be fixed in the open fluid delivery position for an extended period of time when the cassette is not associated with the infusion pump to prevent the tubing from becoming permanently compressed or deformed. Such depression, crimping or deformation can effect the flow of fluids through the tubing resulting in an incorrect amount flowing even when the cassette and infusion pump are both otherwise working properly. The tab member can be held in the open position through the use of a plug that is fitted into the opening 57 between the tab member 107 and the edges of the housing face 50. The plug can then be pulled out to activate the cassette and return the anti-flow valve mechanism to the biased fluid non-delivery position. Latches, catches and hooks associated with the cassette can also be used to hold the tab in the open fluid delivery position for storage and then removed when the cassette is to be used.

In another embodiment, the invention is directed to a reusable cassette that is slipped over the tubing between the fluid reservoir and the patient. The second embodiment has a housing with an essentially rectangular shape and a width configured and dimensioned to fit within an opening in an infusion pump, where the housing has four outside walls, and two faces.

Two of the outside walls define a first and second ends for holding the tubing through which the fluid is directed. The outside walls forming the first and second ends each have a flat wall with an opening configured and dimensioned to fit either the inlet or outlet tubing support which passes through the opening.

The inlet and outlet tubing supports are bushings having openings suitably dimensioned and configured to allow the flexible tubing to be pushed through the bushings, but remain held snugly in position. The bushings prevent the cassette from sliding down the tubing when the cassette is not associated with an infusion pump, and prevents the tubing from slipping when the cassette is associated with a pump.

The infusion pump is configured and dimensioned to be associated with a related cassette. The pump has either an opening into which the cassette can be inserted, or a depression or recess into which the cassette can be seated.

Another embodiment of the invention relates to a fluid delivery system comprising an infusion pump and a cassette with tubing that is configured for engaging the pump mechanism of the infusion pump to accurately and repeatably deliver a fluid to a subject.

The cassette advantageously comprises a housing having first and second ends for holding flexible tubing through which the fluid is directed, wherein the tubing is configured for engaging a pumping mechanism of an infusion pump that provides movement of the fluid through the tubing. The length of tubing is initially held between first and second ends of the cassette prior to engaging the pumping mechanism and preferably in a straight line. The position of the first and second ends of the housing and which at least partially defines a flow path along which the tubing is tensioned for fluid flow therein, and the length of tubing is accurately and repeatably positioned in the flow path with the pumping mechanism stretching the flexible tubing to repeatably tension the tubing to allow correct fluid flow therethrough. The flow path is advantageously and at least partially defined in front of a rigid curved wall of the housing, wherein the fixed, rigid curved wall forms a concave shape opposite the pumping mechanism. When engaged with the pumping mechanism of the pump, this length of tubing is in contact with and positioned between the curved wall and the pumping mechanism upon each engagement of the pumping mechanism and tubing. Upon each engagement of the pumping mechanism and tubing, the pumping mechanism accurately and repeatably stretches the flexible tubing and urges it into contact with the curved wall to tension the tubing to allow correct fluid flow therethrough.

The tubing may be moved into position either when the engagement of the cassette with the pump causes the tubing to move between its initial position and a fluid delivery position, where the tubing is in contact with the curved wall, or alternatively, after engagement of the cassette with the pump, the pumping mechanism moves to urge the tubing to a fluid delivery position in contact with the curved wall.

Either the pumping mechanism or the cassette can be the moveable component, while the other remains in a fixed position. If the pumping mechanism is in a fixed position, the flexible tubing becomes engaged by moving the cassette into contact with the pumping mechanism, whereas if the cassette is in a fixed position when engaged with the infusion pump, the pumping mechanism engages the flexible tubing by moving into contact therewith.

The cassette preferably includes an anti-flow valve mechanism that is initially biased against the tubing in a fluid non-delivery position to prevent flow therethrough, and a member operatively associated with the cassette and anti-flow valve mechanism to overcome the force-applying member bias to allow flow of fluid through the tubing when the housing is engaged with the pump. The housing is configured and dimensioned for engagement with the infusion pump, wherein during or after engagement the member assumes a fluid delivery position to allow flow of the fluid through the tubing, while before or as the cassette is removed from the pump, the member assumes the fluid non-delivery position to prevent flow of fluid through the tubing.

Preferably, the anti-flow valve mechanism is associated with the tubing, cassette or housing or is situated in or near the cassette or housing and comprises a moveable member and a force-applying member, wherein the force applying member in the fluid non-delivery position biases the moveable member against the tubing to prevent flow therethrough; and wherein the moveable member is moveable between the fluid non-delivery position and the fluid delivery position where the force-applying member bias is removed so as to allow fluid flow through the tubing.

The cassette housing is generally configured and dimensioned for engagement with the infusion pump, where the housing has an essentially rectangular shape and is configured and dimensioned to fit within an opening in the infusion pump, or a shape and size configured and dimensioned to be capable of being attached or adjoined to the exterior of the infusion pump, and the housing comprises registration grooves for alignment of the cassette during engagement with the infusion pump. Additionally, the housing includes at least one window adjacent the tubing to allow monitoring or detection of fluid flow therethrough. The housing is made of molded plastic, and the tubing is made of an elastomeric or silicon material.

The tubing may be held between inlet and outlet tubing supports in the housing, wherein each tubing support includes a male junction and a female junction, wherein in the inlet support the male junction is configured and dimensioned to fit inside the tubing and the female junction is configured and dimensioned to receive tubing extending to a fluid supply, and in the outlet support, the male junction is configured and dimensioned to fit inside tubing and the female junction is configured and dimensioned to receive the length of tubing that extends to the subject.

Another embodiment of the invention relates to a fluid delivery system comprising a cassette as described above and an infusion pump. The infusion pump includes a housing having an opening configured and dimensioned to receive the cassette, and a pumping mechanism that engages the flexible tubing and stretches it to position the stretched tubing along the curved wall to provide sufficient tension to allow accurate and repeatable amounts of fluid to flow through the tubing. The combination of the infusion pump and cassette represents yet another embodiment of the invention.

The infusion pump is suitably designed and configured to be associated with the companion cassette having in a first embodiment an opening into which a cassette with suitable dimensions could be inserted, and having in a second embodiment features for attaching and securing the cassette to an exterior surface of the infusion pump. The opening in the pump could be either a slot into which the cassette could be slid edge-wise, or a depression or recess in a face of the pump into which the cassette could be seated. The feature for attaching a cassette to an exterior surface of the infusion pump includes tabs, clips, latches, catches, fasteners, or any combination thereof. The cassette can become engaged with the infusion pump either by insertion into the opening, depression or recess in the pump, or by attaching or adjoining to the infusion pump exterior using the features mentioned above.

The infusion pump typically includes a pumping mechanism that engages the flexible tubing, and stretches the tubing to conform to the flow path by an amount necessary to tension the tubing by a sufficient amount to allow the correct fluid flow through the tubing when the pumping mechanism is engaged. The pumping mechanism stretches the flexible tubing to the same extent each time the cassette becomes associated with the infusion pump.

The infusion pump may also have at least one registration component that engages the registration grooves of the cassette, and at least one sensor in optical alignment with the window of the cassette for monitoring or detection of fluid flow through the tubing.

Another embodiment of the invention relates to a method of accurately and repeatedly dispensing fluid through the tubing of an infusion set which comprises providing the tubing in a cassette that engages an infusion pump for delivery of a fluid to a subject, and providing the cassette with a housing having first and second ends for holding flexible tubing through which the fluid is directed, and with a flow path at least partially defined by a rigid curved wall, with the housing having a length of the tubing which length of tubing engages a pumping mechanism of the infusion pump when associated therewith to be stretched and positioned between the pumping mechanism and the curved wall to provide movement of fluid through the tubing.

In this method, the cassette is used for accurately delivering fluid to a subject via an infusion pump, characterized in that the cassette includes a curved wall such that upon engagement with the pumping mechanism of the infusion pump, the tubing is stretched to be positioned at least partially along the flow path between the pumping mechanism and the curved wall to accurately and repeatably deliver fluid to the subject. The cassette is used to accurately and repeatably deliver a fluid to a subject via an infusion pump.

Yet another embodiment of the invention relates to the use of one of the cassettes, fluid delivery systems and/or pumps disclosed herein for accurately delivering fluid to a subject via tubing of an infusion set. As explained herein, the cassette includes a structure that at least partially defines a flow path, e.g., a curved wall, such that upon engagement with the pumping mechanism of the infusion pump, the tubing is stretched to be positioned along the flow path between the pumping mechanism and the curved wall to accurately and repeatably deliver fluid to the subject.

Referring to FIG. 1, the various components of a preferred cassette 1 according to the invention can be seen. The cassette 1 includes a housing 5, flexible tubing 75 and tubing supports 15 and 35. The flexible tube 75 spans the section formed by the rigid curved wall 25 between the first straight wall section 22 and the second straight wall section 28 of the second outside wall 20. The flexible tubing passes through the openings 24 on either side of the curved wall 25 to meet the inlet tubing support 15 and outlet tubing support 35. The tab member 107 extends from the moveable member 103 of the anti-flow valve mechanism 100 through the opening 57 in the first face 50 sufficiently to engage an activation mechanism associated with the infusion pump. The registration grooves 53 are positioned in the first face 50 to accept raised features of the infusion pump that are configured and dimensioned to fit into the registration grooves in the cassette. The registration grooves can have a variety of lengths, cross-sectional sizes and shapes including but not limited to triangular, square, rectangular, "T," and circular.

Figure 2:
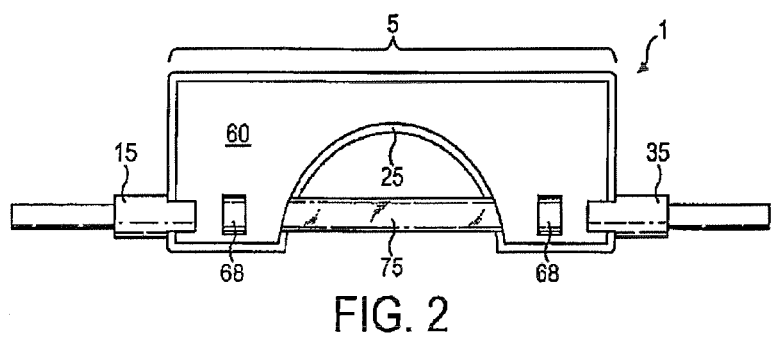
FIG. 2 is a view of the second face of the cassette showing the windows for observing fluid flow.

Referring to FIG. 2, the flexible tubing 75 is situated between the inlet tubing support 15 and outlet tubing support 35. Fluid flow through the flexible tube can be observed through the openings 68 in the second face 60 of the housing 5, when the flexible tubing 75 is pressed against the rigid curved wall 25 by the pump mechanism. This also allows the use of bubble detection or other monitoring devices to assure that the fluid is properly flowing through the tubing 75.

Figure 3A:
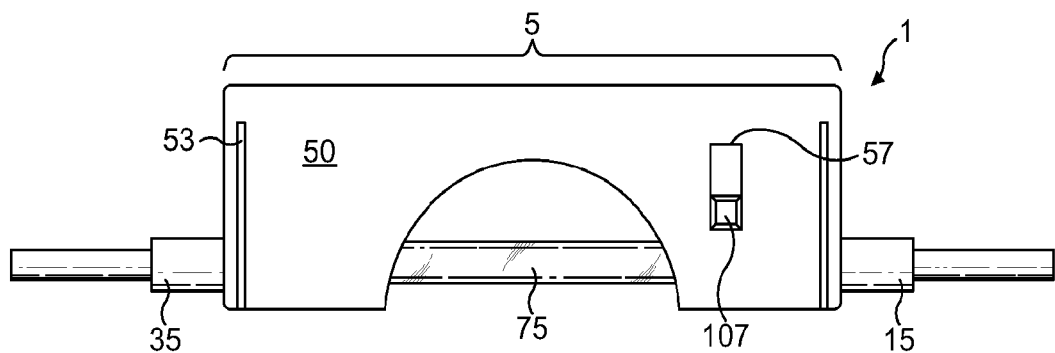
FIG. 3A is a view of the first face of the cassette showing the tab member attached to the anti-flow valve mechanism in the default biased non-delivery position when not inserted in an infusion pump.
Figure 3B:
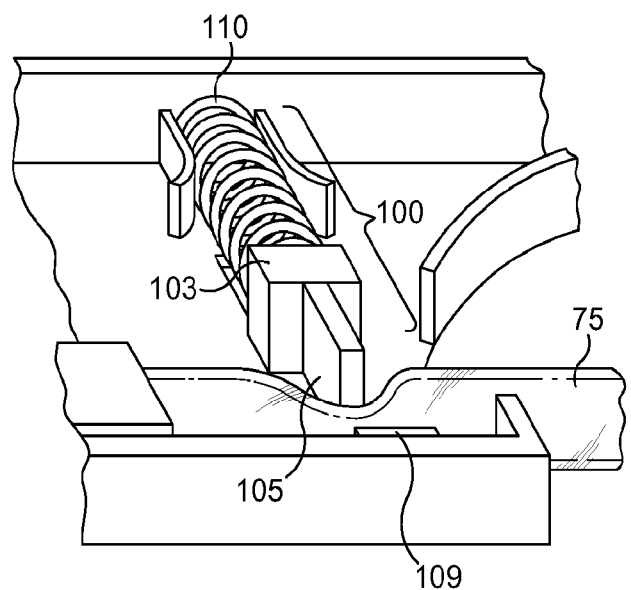
FIG. 3B is an enlarged internal perspective view showing the details of the anti-flow valve mechanism when in the non-delivery position.

Referring to FIG. 3A, the tab member 107 extending through the opening 57 in the first face 50 of the housing 5 is in the default fluid non-delivery position, where, as shown in FIG. 3B, the force-applying member 110 presses against the moveable member 103 causing the pinch head 105 to compress the flexible tubing 75 against the reinforcement 109, thereby preventing fluid flow.

Figure 4A:
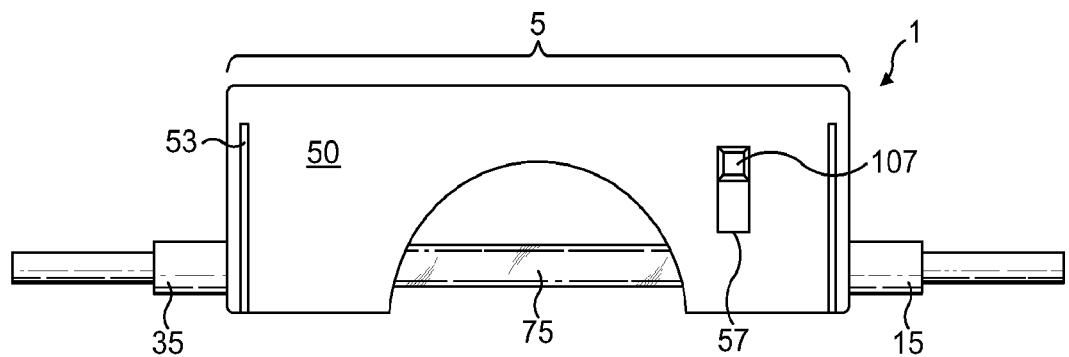
FIG. 4A is a view of the first face of the cassette showing the tab member attached to the anti-flow valve mechanism in the unbiased delivery position when inserted in an infusion pump.
Figure 4B:
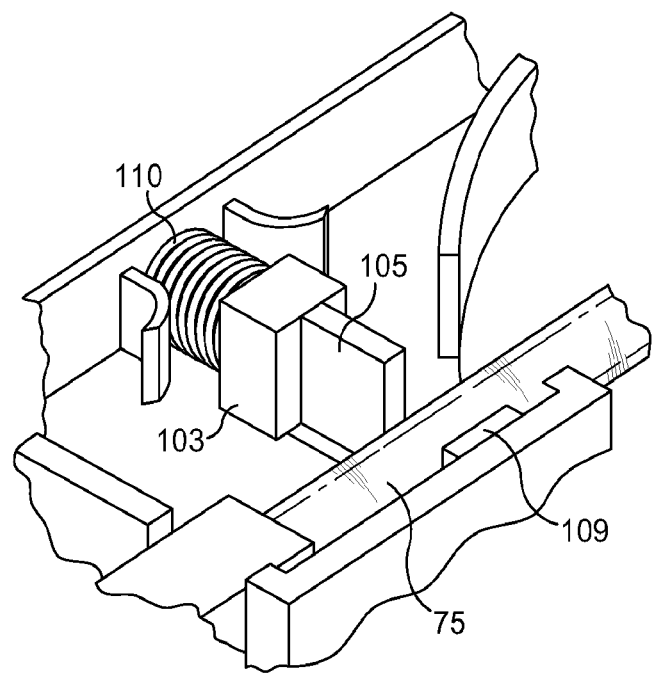
FIG. 4B is an enlarged internal perspective view showing a detail of the anti-flow valve mechanism in the delivery position.

Referring to FIG. 4A, the tab member 107 extending through the opening 57 in the first face 50 of the housing 5 can be moved to the activated fluid delivery position, where, as shown in FIG. 4B, the force-applying member 110 has a reduced dimension and a concomitant increase in stored force by the retraction of the moveable member 103 away from the flexible tubing 75, which releases the force of the pinch head 105 against the flexible tubing and thereby allows free fluid flow. This movement is achieved either automatically when or as the cassette is inserted into a companion infusion pump designed to receive it or by a mechanism in the pump housing itself to move the tab and open the valve only when the pump is activated. The pump includes conventional roller or finger members that, when activated for operation, compress the tube to urge the fluid to flow therethrough. As noted, by the time the pump is activated, the anti-flow valve mechanism is moved to a position where the tubing is not occluded to allow the fluid to flow. When the cassette is disassociated from the pump, or when the pump is deactivated, the anti-flow valve mechanism returns to the non-fluid delivery position to prevent any flow through the tubing, thus avoiding any unintended free-flow conditions.

Figure 5:
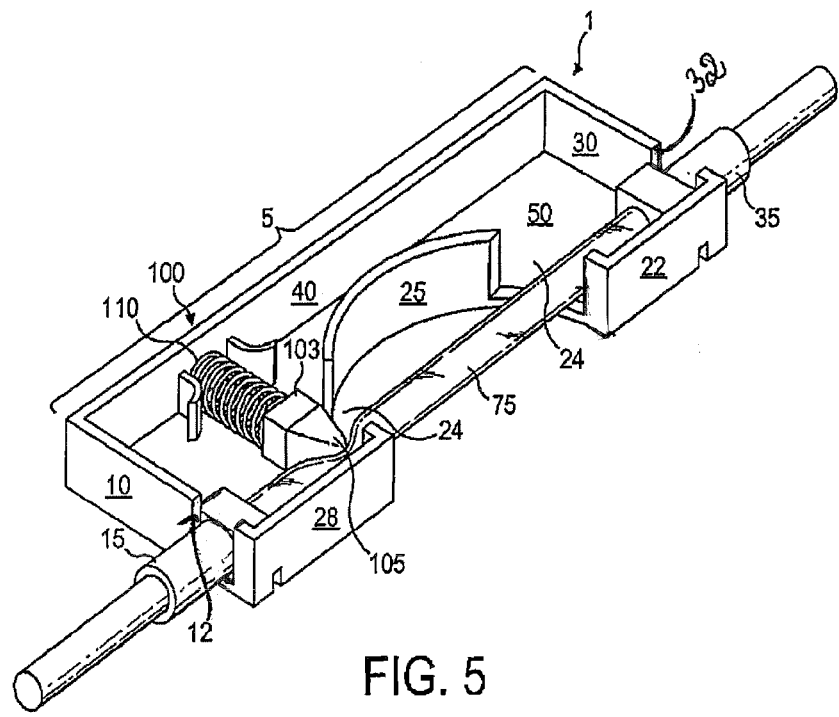
FIG. 5 is a perspective view of the interior assembly of the cassette.

Referring to FIG. 5, the internal arrangement of the anti-flow valve mechanism 100, flexible tubing 75, inlet tubing support 15 and outlet tubing support 35 within the housing 5 can be clearly seen with reference to the rigid curved wall section 25 with openings 24 on either side located between the first straight wall section 22 and the second straight wall section 28 of the second outside wall 20. The force-applying member 110 is positioned between the fourth straight wall section 40 and the moveable member 103, thereby pressing the pinch head 105 against the flexible tubing 75, so the tubing is pressed closed against a reinforcement 109 adjacent to the first straight wall section 22 of the second outside wall 20.

The anti-flow valve mechanism is preferably located on the inlet side of the cassette as depicted in the figures, however it could also be located on the outlet side.

The housing 5 is preferably rectangular with dimensions and a width suitable to fit into an infusion pump, although the housing could also have other shapes if necessary to fit within the pump. The housing is made of a material suitable for use in a medical environment without breaking or causing contamination, and can be either disposable or capable of being cleaned, autoclaved or sanitized for subsequent reuse. Generally, an engineering plastic is used for this purpose. The housing allows easy and secure placement of the force-applying member, moveable member and tubing supports inside the closed housing. The housing may be formed of two or more molded pieces that are later assembled and sealed with the other components inside. The housing may be permanently sealed, or be held together by tabs, clips, latches, catches, fasteners, or any combination thereof to allow for later access to the internal components for cleaning or replacement.

The fourth outside wall 40 is preferably a solid flat face that can be easily pushed against when inserting the cassette 1 into or securing it to the exterior of an infusion pump, although it could have other contours, textures, openings, or features.

The second outside wall 20 has both straight and curved sections configured and dimensioned to engage the infusion pump and pumping mechanism. The rigid curved wall 25 is configured and dimensioned to accept the infusion pump wheel and rollers, so there is free rotation of these elements when the pump is in operation, and the rollers can compress the flexible tubing 75 properly to create the pumping action. The cassette is designed so that the curved wall is sufficiently strong and rigid to retain its shape as the rollers or fingers of the infusion pump repeatedly press against the flexible tubing compressing it against the wall. The edges of the curved wall at the openings 24 are preferably beveled to avoid corners that can pinch the flexible tubing when the cassette 1 is inserted into the infusion pump and the infusion pump wheel and rollers push the flexible tubing back against the curved impression.

The openings 24 on either side of the rigid curved wall section are suitably sized, configured and dimensioned to allow the flexible tubing 75 to follow the contour of the curved impression without completely pinching off flow by pressing against either edge of the curve when the cassette is inserted into the infusion pump, and are aligned with the flexible tube when it is fixed in the straight-through position between the two tube supports, when the housing is not inserted in the infusion pump.

The fixed position and length of the flexible tubing in coordination with the configuration and dimensions of the cassette and pump produces the same amount of tension in the flexible tubing each and every time the cassette is engaged by the pumping mechanism. Engagement of the pumping mechanism with the cassette then creates suitable tension in the flexible tubing to allow a correct and accurate amount of fluid flow when the pump is operating.

In one embodiment, the first outside wall 10 has an opening 12 configured and dimensioned to hold an inlet tubing support 15 which passes through the opening, and the third outside wall 30 has an opening 32 configured and dimensioned to hold an outlet tubing support 35 which passes through the opening.

In another embodiment, the tubing supports are molded as part of the first and third outside walls to form a single integral part of the housing wall.

In either embodiment, the tubing supports 15 and 35 can have the form of either adaptors that connect a separate length of flexible tubing, which is fixed between the adaptors, with different tubing on the inlet and outlet sides, or bushings that have an inner diameter that is suitably dimensioned to be pushed over a unitary piece of flexible tubing and hold it snugly between the two bushings to prevent the cassette from sliding down the tubing when the cassette is not associated with the infusion pump.

The tubing supports can be made of a transparent material that allows the fluid flow to be observed, and any bubbles or obstructions to be detected or monitored. Alternatively, as described herein below, windows may be provided in the housing for this purpose.

When not a molded part of the housing, the adaptor used to connect different pieces of tubing preferably has a cube-shaped central section that is sized, configured and dimensioned to be held in place within the housing at the first outside wall opening 12 or third outside wall opening 32, with one round male junction extending from the central section into the housing having an outer diameter over which the flexible tubing can be pushed to form an airtight seal, and one round female junction extending from the central section out of the housing 5 with an inner diameter into which an intravenous line can be pushed to form an airtight seal. The male junction can have barbs to better secure the flexible tubing. While this arrangement is preferred, other designs can be used for holding the tubing in the manner and position described herein.

When not a molded part of the housing, the bushing used to hold a length of flexible tubing preferably has a cube-shaped central section that is sized, configured and dimensioned to be held in place within the housing at the first outside wall opening 12 or third outside wall opening 32, with an interior stress-relief portion that extends from the central section into the housing, and an exterior stress-relief portion that extends from the central portion out from the housing. A hole having a diameter dimensioned to fit tightly over the flexible tubing passing through the bushing. The bushings hold the flexible tubing 75 snugly so the cassette does not slide down the tubing if allowed to hang from it, and prevents a change in tension in the flexible tubing due to the action of the infusion pump pulling on the tubing when the cassette is inserted in the infusion pump.

The flexible tubing 75 can be made of any elastomeric material which is preferably transparent flexible medical grade material such as silicone, which is most preferred.

The anti-flow valve mechanism 100 comprises a moveable member 103 that is operatively associated with a force-applying member 110 at a face opposite a pinch head 105. The moveable member face in contact with the force-applying member is suitably dimensioned to allow sufficient contact between the force-applying member and the moveable member to transfer the force of the force-applying member to the pinch head. The face of the moveable member preferably has a raised or recessed feature that can seat the force-applying member to thereby keep the force-applying member aligned and prevent the loss of contact between the two components.

The moveable member 103 preferably has wider dimensions at the force-applying member contact end and narrower dimensions at the pinch head 105 end, and a tab member 107 extending from a face of the moveable member 103 perpendicular to the axis of the force-applying member 110 and pinch head 105. The pinch head can have different shapes such as a "T", "U", "V" or a wedge. Such shapes concentrate the force of the force-applying member to a smaller area to improve the closing action on the flexible tubing when in the default non-delivery position. The shape of the end of the pinch head in contact with the tubing can have either a flat face, curved face with a range of radii, or a sharp corner, where the curved face is the preferred embodiment. Such curved end faces reduce the wear on the portion of tubing that becomes crimped when the moveable member is in the non-delivery position.

The pinch head 105 presses against one side of the flexible tubing 75 and compresses it against a reinforcement 109 on the opposite side thereby closing the tubing and preventing any free fluid flow when the cassette is not inserted in an infusion pump.

The tab member 107 extends from the moveable member 103 perpendicular to the pinch head through an opening 57 in the first face 50 of the housing 5. The tab member 107 is sufficiently long to extend above the first face 50 of the housing 5, and engage an activation mechanism on the infusion pump, which would cause the moveable member 103 to retract and increase the stored force in the force-applying member 110 when the cassette 1 is associated with the infusion pump. The moveable member 103 is made of a tough impact resistant material sufficient to withstand repeated engagement of the tab with the infusion pump activation mechanism while resisting the force of the force-applying member when the cassette is associated with the infusion pump, as well as contact between the pinch head and the flexible tubing when the cassette is disassociated from the pump.

The force-applying member 110 is positioned between the fourth outside wall 40 and the moveable member 103, which thereby translates the force through the pinch head 105 to compress the flexible tubing 75. The force-applying member has an increase in stored force when the cassette 1 is associated with an infusion pump, and the contact between an activation mechanism and the tab member 107 causes the anti-flow valve mechanism 100 to retract. The force-applying member is preferably a round compression spring made of stainless steel or another material suitable for use in a medical environment, however it may also be a leaf spring, lever or elastic element. The force-applying member has sufficient strength to completely pinch the flexible tubing closed when the tab is released, but can be compressed when the cassette is associated with the infusion pump. The force is applied to the tubing through the pinch head, which can have different shapes such as a "T", "U", "V" or a wedge. These shapes result in a smaller contact surface between the pinch head and the flexible tubing, and thereby concentrates the force exerted by the force-applying member.

Figure 6:
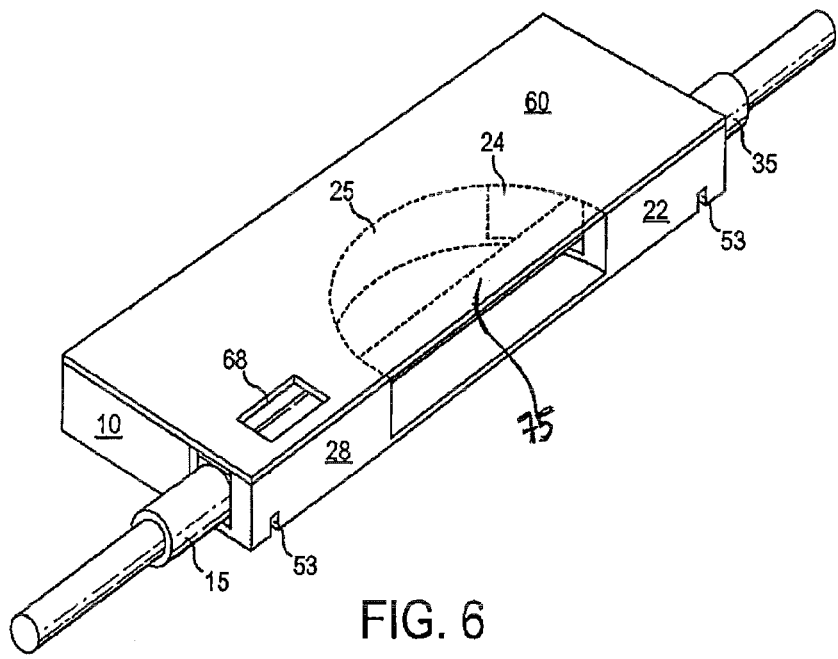
FIG. 6 is a perspective view of the cassette illustrating another embodiment of a housing without portions of a first and second face cut away to create the open area.

Referring to FIG. 6, the first face 50 of the housing 5 is preferably rectangular in shape to match the dimensions of the outside walls of the housing, but could have a curved cut-away portion that is configured and dimensioned to match the straight wall sections 22, 28 and curved wall section 25 of the second outside wall 20 to form an open area in conjunction with the cut-away portion of the second face thereby exposing the tubing 75 (see FIG. 1). The first face 50 has an opening 57 suitably positioned to allow the tab member 107 of the piston 103 to extend through the opening and above the first face. The first face 50 has two registration grooves 53 configured and dimensioned to receive a raised feature on the infusion pump. The grooves 53 polarize the cassette 1 so it can only be inserted one way into the infusion pump. The preferred shape of each of the grooves 53 is a straight rectangle.

The second face 60 of the housing 5 is preferably rectangular in shape to match the dimensions of the outside walls of the housing (see FIG. 6), but may have a curved cut-away portion that is configured and dimensioned to match the straight wall sections 22, 28 and curved wall section 25 of the second outside wall 20 to form an open area in conjunction with the cut-away portion of the second face thereby exposing the tubing 75 (see FIG. 1). The second face 60 has two openings 68 placed on opposite sides of the curved cut-away portion aligned with the position of the flexible tube when held in a straight-through position by the inlet 15 and outlet 35 tubing supports. These openings allows observation of the fluid flow and the presence of bubbles or obstructions.

Either of the faces 50, 60 or the wall 40 can have features for holding the force-applying member in its proper position.

Figure 7A:
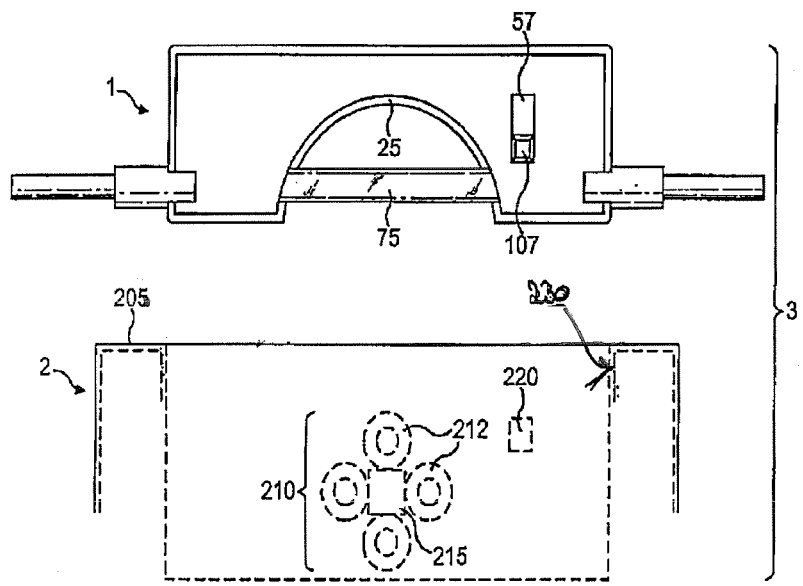
FIG. 7A-7D is a series of views showing the stages of engagement of the cassette tubing and tab member with the pump mechanism and engagement mechanism for insertion of a cassette into a diffusion pump.
Figure 7B:
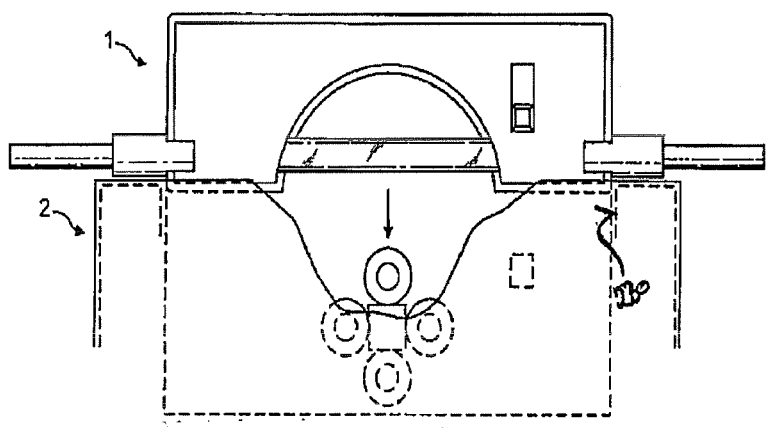

Referring to FIGS. 7A-7D, the cassette and infusion pump comprise the cassette/pump fluid delivery system 3. Referring to FIG. 7A, the infusion pump 2 comprises a housing 205 containing a pump mechanism 210 that engages the flexible tubing 75 of the cassette 1, an activation mechanism 220 that can engage the tab member 107 on the cassette, and optionally a feature for attaching or adjoining a cassette to the housing (not shown).

The pump housing 205 is configured and dimensioned so as to receive and engage with the cassette 1. Engagement can be achieved by either insertion of the cassette 1 into an opening 230, recess or depression in one of the faces of the housing, where the opening 230, recess or depression is configured and dimensioned to accept the cassette, or by attachment or adjoining of the cassette to a position on the exterior of the of the housing. The cassette can be attached or adjoined and secured by some feature such as tabs, clips, latches, catches, fasteners, or any combination thereof.

The pump mechanism 210 comprises one or more rollers 212 or fingers arranged around a central hub 215 that can rotate freely, and is configured and dimensioned to fit within the area defined by the rigid curved wall 25 of the cassette when engaging the flexible tubing. The pump mechanism 210 stretches and applies tension to the tubing 75 by pressing the tubing between the rollers 212 or fingers of the pump mechanism 210 and the rigid curved wall of the cassette 25. The stretching and tensioning occurs because the length of tubing that is initially held between the ends of the cassette in a straight line is made to take a longer path when engaged by the pump mechanism (see FIG. 7C). This engagement conforms the tubing to the space between the rigid curved wall and the pump mechanism (see FIG. 7D). The length of tubing 75 is in contact with and compressed between the curved wall 25 and the pumping mechanism rollers 212, so the pump can deliver fluid through the tube. The pumping mechanism creates the same amount of tension in the flexible tubing each and every time it is engaged with the cassette, and this tension allows a correct and accurate amount of fluid to flow through the tubing when the pumping mechanism is activated. The positioning, tensioning and amount of fluid flow are repeatable each and every time a the cassette and pump are engaged. The action of the pump mechanism causes a controlled flow of fluid of a correct and accurate amount through the flexible tubing, and restricts the flow of fluid through the tubing when stopped.

The pumping mechanism can move to engage the tubing automatically when the cassette is engaged with or inserted into the pump through the use of a sensor or trigger that detects the presence of the cassette. Movement of the pumping mechanism from a retracted position to a extended position that engages the flexible tubing can be achieved using a motor, piston or similar drive mechanism. The pumping mechanism may follow a linear or circular path between an initial position and the position where the tubing is compressed between the curved wall 25 and the pumping mechanism rollers 212. The pumping mechanism preferably moves in the plane of the tubing, so that the rollers contact the tubing at a proper angle and stretch the tubing the proper amount, such that the tubing is accurately positioned in contact with and between the curved wall and the pumping mechanism.

In another embodiment, the pumping mechanism can rotate around an axis that is parallel to the axis of the tubing, such that the pumping mechanism swings up from a position perpendicular to the plane of the cassette to a position in the plane of the tubing.

The infusion pump 2 has an activation mechanism for engaging the tab member 107 of the anti-flow valve mechanism 100 that causes the tab member 107 to move between the fluid non-delivery position (see FIG. 3A), and a fluid delivery position (see FIG. 3B) to allow fluid flow through the tubing.

Figure 7C:
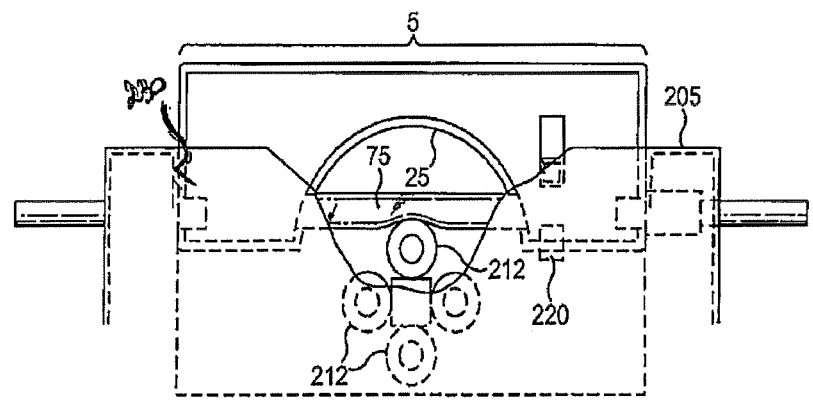
Figure 7D:
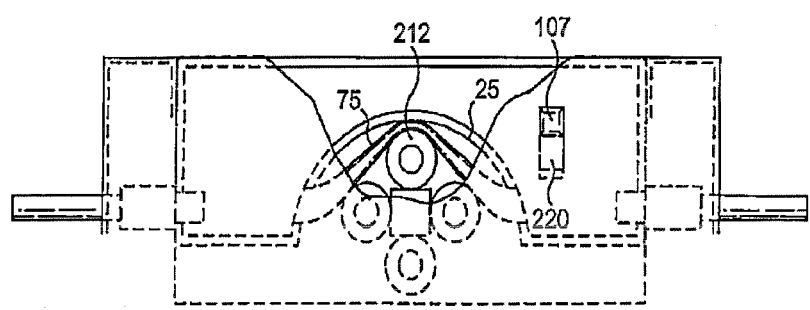

The activation mechanism can comprise either a protrusion or wall 220 that makes contact with the tab member 107 as the cassette engages the pump to move the tab to the fluid delivery position and to hold it there after the cassette is inserted into the infusion pump (see FIGS. 7C-7D).

The protrusion or wall 220 extends from the housing of the pump and is suitably configured and dimensioned to extend into the path of the tab member, thereby preventing the tab from moving more than a specific distance into the opening 230 of the pump housing 5 when the cassette is inserted into the pump (see FIGS. 7C-7D). The protrusion can be a raised feature that is essentially the same size as the tab member located in the path of the tab member. The protrusion can have any shape that can block the motion of the tab member, but preferably is wedge-shaped with the flat face contacting the tab and the wedge sloping back away from the contact face. This arrangement provides the maximum contact surface between the tab 107 and activation mechanism 220 with sufficient strength and durability to withstand repeated insertion of cassettes without wearing or breaking The protrusion should be suitably sized to avoid interference with the actual insertion of the cassette into the infusion pump. The wall extends perpendicularly across the path of the tab member, wherein the length of the wall perpendicular to the path of the tab member is at least greater than the width of the tab member, and could extend across the entire length of the opening in the infusion pump housing.

In another embodiment, the activation mechanism may be an arm or a multiple component assembly configured and dimensioned to cause the tab member to move between the fluid non-delivery position and a fluid delivery position. The activation mechanism could move the tab member as the cassette is engaged with or inserted into the pump, after the cassette is engaged with or inserted into the pump, or as or after the pumping mechanism engages the flexible tubing of the cassette. The activation mechanism can move independently of both the cassette and the pumping mechanism when moving the tab member. The sequence of engaging the cassette with the infusion pump, engaging the pumping mechanism, and moving the anti-flow valve mechanism between the delivery and non-delivery positions as well as the reverse sequence of disassociating the cassette can be altered to accommodate the particular requirements of the fluid delivery system application.

The movement of the activation mechanism may be triggered by engagement of the cassette with the pump or pumping mechanism, activation of the pumping mechanism, or may be triggered automatically by a separate triggering event, or manually by a user at some chosen time. Where engagement of the pumping mechanism with the cassette prompts the activation mechanism to push the tab member to the fluid delivery position, the movement of the tab member may be sufficiently delayed to allow the pumping mechanism rollers 212 to pinch the tubing 75 closed before the anti-flow valve mechanism 100 is moved to the fluid delivery position. This allows compression of the flexible tubing at one location before releasing the compression at another location, and thereby prevents any interim leakage though the tubing.

Engagement of the activation mechanism with the tab member can be initiated automatically upon engagement with or insertion of the cassette into the pump through the use of a sensor, switch or trigger. The engagement of the activation mechanism with the tab member may also be initiated manually by a user starting the pump or independently activating a sensor, switch or trigger. Movement of the activation mechanism to engage the tab member can be achieved using a drive mechanism such as a motor, piston or similar device. The drive mechanism can move the activation mechanism directly, or it may move the pumping mechanism directly and the activation mechanism through association with the pumping mechanism.

The removal of the cassette from the pump can automatically disengage the activation mechanism and releases the tab member so that the force-applying member returns to the biased fluid non-delivery position to prevent flow of fluid through the tubing. Alternatively, when the infusion pump activation mechanism engages the tab member 107 after the cassette is inserted into the infusion pump to allow compression of the flexible tubing by the pumping mechanism rollers 212 before moving the anti-flow valve mechanism 100 to the fluid delivery position, the activation mechanism would disengage and release the tab member 107 so that the force-applying member 110 returns the moveable member 103 to the fluid non-delivery position to prevent flow of fluid through the tubing before compression by the rollers is released and the cassette is removed from the pump. This prevents any interim leakage though the tubing.

The sequence of associating the cassette with the infusion pump, engaging the pumping mechanism, and moving the anti-flow valve mechanism between the delivery and non-delivery positions as well as the reverse sequence of disassociating the cassette can be altered to accommodate the particular requirements of the fluid delivery system application.

The infusion pump can also have one or more registration components that engages the registration grooves of the cassette The registration components can be pins, raised tracks or other raised features that are configured and dimensioned to fit into the registration grooves in the cassette face to prevent the cassette from being associated with the pump in an incorrect manner or orientation. The registration grooves can have a variety of lengths, cross-sectional sizes and shapes including but not limited to triangular, square, rectangular, "T," and circular.

These descriptions is only illustrative of the preferred embodiments of the present invention, and are not meant to restrict the invention in any way. Other modifications and alternative embodiments will be apparent to those skilled in the art.

What is claimed is:

1. A cassette for engagement with an infusion pump for delivery of a fluid to a subject comprising:
   a housing having first and second ends for holding a flexible tubing through which the fluid is directed, the flexible tubing is configured for engaging a pumping mechanism of the infusion pump that moves the fluid through the flexible tubing;
   an anti-flow valve mechanism that is biased against the flexible tubing in a fluid non-delivery position to prevent flow therethrough;
   a member operatively associated with the anti-flow valve mechanism to overcome the bias to allow flow of fluid through the flexible tubing when the housing is engaged with the infusion pump;
   the housing is configured and dimensioned for engagement with the infusion pump, wherein during or after engagement, the member assumes a fluid delivery position to allow flow of the fluid through the flexible tubing, while before or as the cassette is removed from the infusion pump, the member assumes the fluid non-delivery position to prevent flow of fluid through the flexible tubing, the member is a tab member that is moveable between the fluid non-delivery position and the fluid delivery position, and the tab member is designed to engage with an activation mechanism of the infusion pump, wherein the housing has a first face, a second face, and four outside walls, wherein one outside wall has two straight wall sections and a curved wall section between the two straight wall sections, wherein the tab member protrudes through an opening in the first face, and the first face is fixedly connected to all four outside walls, wherein the anti-flow valve mechanism is located at a position selected from the group consisting of 1) associated with the flexible tubing, the cassette or the housing, and 2) situated in or near the cassette or housing;

the anti-flow valve mechanism comprises a movable member and a force applying member; and prior to engagement of the housing with the infusion pump, the tab member and the moveable member are in the fluid non-delivery position whereas during or after engagement, the tab member overcomes the bias and moves the movable member to the fluid delivery position, wherein the tab member extends from a face of the movable member and is movable in a direction perpendicular to an axis parallel to a main extension direction of the force applying member, wherein the tab member contacts the face of the movable member.

2. The cassette of claim 1, wherein the tab member moves the moveable member to the fluid delivery position as the cassette engages the infusion pump to allow the flow of fluid through the flexible tubing, and as the cassette is removed from the infusion pump, the tab member is released so that the moveable member returns to the fluid non-delivery position to prevent the flow of fluid through the flexible tubing such that movement of the tab member between the fluid non-delivery position and the fluid delivery position changes the biasing of the force-applying member.

3. The cassette of claim 1, wherein the tab member moves the moveable member to the fluid delivery position after the cassette engages the infusion pump to allow the flow of fluid through the flexible tubing, and before the cassette is removed from the infusion pump, the tab member is released so that the moveable member returns to the fluid non-delivery position to prevent the flow of fluid through the flexible tubing such that movement of the tab member between the fluid non-delivery position and the fluid delivery position changes the biasing of the force-applying member.

4. The cassette of claim 1, wherein the housing has an essentially rectangular shape and is configured and dimensioned to fit within an opening in the infusion pump, and a length of the flexible tubing is initially held between the ends of the cassette in a straight line and in front of the curved wall section of the housing such that when engaged with the pumping mechanism of the infusion pump, the length of the flexible tubing is accurately positioned in contact with and between the curved wall section and the pumping mechanism.

5. The cassette of claim 1, wherein the housing comprises registration grooves for alignment of the cassette during engagement with the infusion pump, and the housing includes at least one window adjacent the flexible tubing to allow monitoring or detection of fluid flow therethrough.

6. The cassette of claim 1, wherein the housing is made of molded plastic, the flexible tubing is made of an elastomeric or silicone material, and the flexible tubing is held between inlet and outlet tubing supports in the housing, each tubing support includes a male junction and a female junction, in the inlet support the male junction is configured and dimensioned to fit inside the flexible tubing and the female junction is configured and dimensioned to receive the flexible tubing extending to a fluid supply, and in the outlet support, the male junction is configured and dimensioned to fit inside the flexible tubing and the female junction is configured and dimensioned to receive the length of the flexible tubing that extends to the subject.

7. A cassette for engagement with an infusion pump for delivery of a fluid to a subject comprising:

a housing having first and second ends for holding a flexible tubing through which the fluid is directed, the flexible tubing is configured for engaging a pumping mechanism of the infusion pump that moves the fluid through the flexible tubing;

an anti-flow valve mechanism that is biased against the flexible tubing in a fluid non-delivery position to prevent flow therethrough;

a member operatively associated with the anti-flow valve mechanism to overcome the bias to allow flow of fluid through the flexible tubing when the housing is engaged with the infusion pump;

the housing is configured and dimensioned for engagement with the infusion pump, wherein during or after engagement, the member assumes a fluid delivery position to allow flow of the fluid through the flexible tubing, while before or as the cassette is removed from the infusion pump, the member assumes the fluid non-delivery position to prevent flow of fluid through the flexible tubing, the member is a tab member that is moveable between the fluid non-delivery position and the fluid delivery position, and the tab member is designed to engage with an activation mechanism of the infusion pump, wherein the housing has a first face, a second face, and four outside walls, wherein one outside wall has two straight wall sections and a curved wall section between the two straight wall sections, wherein the tab member protrudes through an opening in the first face and the first face is fixedly connected to all four outside walls, wherein the anti-flow valve mechanism is located at a position selected from the group consisting of 1) associated with the flexible tubing, the cassette or the housing and 2) situated in or near the cassette or housing, the anti-flow valve mechanism comprises a movable member and a force applying member, wherein the force-applying member includes a compression spring, and the moveable member of the anti-flow valve mechanism comprises a pinch head that has a relatively larger cross-sectional surface that contacts the force-applying member and a relatively narrower cross-sectional surface contacting the flexible tubing that concentrates the force of the force-applying member against the flexible tubing, and prior to engagement of the housing with the infusion pump, the tab member and the moveable member are in the fluid non-delivery position whereas during or after engagement, the tab member overcomes the bias and moves the movable member to the fluid delivery position, wherein the tab member extends from a face of the movable member in a direction perpendicular to an axis parallel to a main extension direction of the force applying member so that the tab member contacts the face of the movable member.

8. A fluid delivery system comprising:
a cassette for engagement with an infusion pump for delivery of a fluid to a subject comprising a housing having first and second ends for holding a flexible tubing through which the fluid is directed, the flexible tubing is configured for engaging a pumping mechanism of the infusion pump that moves the fluid through the flexible tubing, an anti-flow valve mechanism that is biased against the flexible tubing in a fluid non-delivery position to prevent flow therethough, a tab member operatively associated with the anti-flow valve mechanism to overcome a force-applying member bias to allow flow of fluid through the flexible tubing when the housing is engaged with the infusion pump, and the housing is configured and dimensioned for engagement with the infusion pump, wherein during or after engagement, the tab member assumes a fluid delivery position to allow flow of the fluid through the flexible tubing, while before or as the cassette is removed from the infusion pump, the tab member assumes the fluid non-delivery position to prevent flow of fluid through the flexible tubing,
wherein the anti-flow valve mechanism is located at a position selected from the group consisting of 1) associated with the flexible tubing, the cassette or the housing, and 2) situated in or near the cassette or housing;
the anti-flow valve mechanism comprises a movable member and a force applying member; and
prior to engagement of the housing with the infusion pump, the tab member and the moveable member are in the fluid non-delivery position whereas during or after engagement, the tab member overcomes the bias and moves the movable member to the fluid delivery position, wherein the tab member extends from a face of the movable member in a direction perpendicular to an axis parallel to a main extension direction of the force applying member member, so that the tab member contacts the face of the movable member; and
the infusion pump comprises a pump housing having an opening configured and dimensioned to receive or engage with the cassette and an activation mechanism for engaging the tab member and thereby causing the tab member to move between the fluid non-delivery position and the fluid delivery position to allow fluid flow through the flexible tubing, and the pumping mechanism that engages the flexible tubing to provide movement of fluid through the flexible tubing only when the cassette is engaged with the infusion pump, the infusion pump detects engagement of the cassette, and the tab member is in the fluid position, wherein the housing has a first face, a second face, and four outside walls, wherein one outside wall has two straight wall sections and a curved wall section between the two straight wall sections, wherein the tab member protrudes through an opening in the first face, and the first face is fixedly connected to all four outside walls, wherein the activation mechanism is configured so that the activation mechanism can be moved independently from the cassette and the pumping mechanism when moving the tab member and when the cassette is engaged with the infusion pump.

9. The system of claim 8, wherein the pumping mechanism stretches the flexible tubing by an amount necessary to tension the flexible tubing by a sufficient amount to allow a correct fluid flow through the flexible tubing each time the pumping mechanism and the cassette are engaged.

10. The system of claim 9, wherein the activation mechanism causes the tab member to move between the fluid non-delivery position and the fluid delivery position either as the cassette engages the infusion pump or after the cassette engages the infusion pump.

11. The system of claim 8, wherein the pumping mechanism is in a fixed position and the flexible tubing becomes engaged therewith by moving the cassette into contact with the pumping mechanism, or the cassette is in a fixed position when associated with the infusion pump and the pumping mechanism engages the flexible tubing by moving into contact therewith.

12. The system of claim 8, wherein the housing comprises registration grooves for alignment of the cassette during engagement with the infusion pump, the housing has an essentially rectangular shape and is configured and dimensioned to fit within an opening in the infusion pump, and the infusion pump comprises at least one registration component that engages the registration grooves of the cassette, and at least one sensor that is in optical alignment with the window for monitoring or detection of fluid flow through the flexible tubing.

13. A method for providing a fluid delivery system according to claim 9 comprising providing the flexible tubing in a cassette that engages an infusion pump for delivery of a fluid to a subject, and providing the flexible tubing or the cassette with an anti-flow valve mechanism comprising a moveable member and a force-applying member wherein, when not engaged with the infusion pump, the moveable member and the force-applying member are maintained in a fluid non-delivery position with the force-applying member biasing the moveable member against the flexible tubing to prevent flow therethrough, and when or after the cassette engages the infusion pump, the force-applying member is moved by the infusion pump to a fluid delivery position where the moveable member is not biased against the tubing to allow fluid to flow therethrough, the cassette includes a housing having first and second ends for holding the flexible tubing through which the fluid is directed, the housing holding a length of the flexible tubing that engages a pumping mechanism of the infusion pump that moves fluid through the flexible tubing, and a tab member operatively associated with the housing and the anti-flow valve mechanism such that movement of the tab member between the fluid non-delivery position and the fluid delivery position changes the biasing of the force-applying member, wherein the tab member extends from a face of the movable member in a direction perpendicular to an axis parallel to a main extension direction of the force applying member, member, so that the tab member contacts the face of the movable member, and the tab member is designed to engage with an activation mechanism of the infusion pump, wherein the housing has a first face, a second face, and four outside walls, wherein one outside wall has two straight wall sections and a curved wall section between the two straight wall sections, wherein the tab member protrudes through an opening in the first face, and the first face is fixedly connected to all four outside walls, wherein the activation mechanism can be moved independently from the cassette and the pumping mechanism when moving the tab member and when the cassette is engaged with the infusion pump.

14. The method of claim 13, wherein the tab member moves the moveable member to the fluid delivery position as the cassette engages the infusion pump to allow fluid flow through the flexible tubing and, as the cassette is removed from the pump, the tab member is released so that the moveable member returns to the fluid non-delivery position.

15. The method of claim 13, wherein the tab member moves the moveable member to the fluid delivery position after the cassette engages the infusion pump to allow fluid flow through the flexible tubing and before the cassette is removed from the infusion pump, the tab member is released so that the moveable member returns to the fluid non-delivery position.

16. An anti-flow valve mechanism preventing free-flow of fluid through a tubing of an infusion set, the anti-flow valve mechanism having a housing and comprises a moveable member and a force-applying member wherein, when not engaged with a pump, the moveable member and the force-applying member are maintained in a fluid non-delivery position with the force-applying member biasing the moveable member against the tubing to prevent flow therethrough, and when or after the cassette engages the pump, the force-applying member is moved by the pump to a flow delivery position where the moveable member is not biased against the tubing to allow fluid to flow therethrough, and a tab member extends from a face of the movable member in a direction perpendicular to an axis of the force-applying member, so that the tab member contacts the face of the moveable member, wherein the axis of the force-applying member is an axis parallel to a main extension direction of the force-applying member, wherein the force-applying member is a spring.

* * * * *